United States Patent [19]

Vial et al.

[11] Patent Number: 5,679,634
[45] Date of Patent: Oct. 21, 1997

[54] USE OF DIHYDROBENZOFURANONES AS PERFUMING INGREDIENTS

[75] Inventors: Christian Vial, Geneva; Pierre-Alain Blanc, Crassier, both of Switzerland

[73] Assignee: Firmenich S.A., Geneva, Switzerland

[21] Appl. No.: 571,862

[22] PCT Filed: Mar. 27, 1995

[86] PCT No.: PCT/IB95/00206

§ 371 Date: Jan. 4, 1996

§ 102(e) Date: Jan. 4, 1996

[87] PCT Pub. No.: WO95/30667

PCT Pub. Date: Nov. 16, 1995

[30] Foreign Application Priority Data

May 9, 1994 [CH] Switzerland ................ 144194

[51] Int. Cl.$^6$ ........................ A61K 7/46
[52] U.S. Cl. ............ 512/13; 549/307; 252/174.11; 252/8.6
[58] Field of Search .............. 512/13; 549/307; 252/174.11, 8.6

[56] References Cited

U.S. PATENT DOCUMENTS

| | | | |
|---|---|---|---|
| 3,144,467 | 8/1964 | Houlihan | 512/13 |
| 3,258,400 | 6/1966 | Houlihan | 512/13 |
| 3,652,666 | 3/1972 | Farge et al. | 549/307 |
| 4,252,817 | 2/1981 | Closse et al. | 307/83 |
| 5,354,735 | 10/1994 | Demole et al. | 512/8 |

FOREIGN PATENT DOCUMENTS

| | | | |
|---|---|---|---|
| 0 041 122 | 12/1981 | European Pat. Off. . | |
| 2257141 | 1/1993 | United Kingdom | 549/307 |
| WO94/12143 | 6/1994 | WIPO . | |

OTHER PUBLICATIONS

K. Takahashi et al. "Usnic Acid. XV. Alkaline Degradation of Usnic Acid", *Chemical and Pharmaceutical Bulletin*, vol. 28, No. 1, 1980, pp. 177–180.

F.M. Dean et al., "Usnic Acid. Part XI. A Synthesis of 7–Acetyl–4:6–dihydroxy–e:5–dimethylcoumara n–2–one", *Journal of the Chemical Society*, 1955, Letchworth, pp. 2166–2170.

O. Piccolo et al. "A simple route to benzofuran–2(3H)–ones", *Chemical Abstracts*, vol. 104, No. 7, 1986, pp. 508, Abstract No. 50742e.

O. Piccolo et al., "A Simple Route to Benzofuran–2(3HO–ones)," *J. Chem. Research* (S), 1985, pp. 258–259.

O. Piccolo et al., "A Facile and Efficient synthesis of (o–Hydroxyarll)–glycolic Acid Derivatives", *Communications*, 1984, pp. 760–763.

*Primary Examiner*—James H. Reamer
*Attorney, Agent, or Firm*—Pennie & Edmonds

[57] ABSTRACT

We describe the use of substituted (3H)-benzo[b]furan-2-ones, namely with alkyl groups, for the preparation of perfuming compositions and perfumed articles, to which these compounds impart odor notes of the lactonic, coumarinic and fruity, or yet musky, type.

12 Claims, No Drawings

USE OF DIHYDROBENZOFURANONES AS PERFUMING INGREDIENTS

TECHNICAL FIELD

The present invention relates to the field of perfumery. It concerns, more particularly, the use, as a perfuming ingredient, of a compound of formula

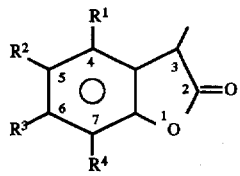

wherein a. symbols $R^1$ to $R^4$ are identical or different and each represents a hydrogen atom, a saturated or unsaturated, linear or branched, alkyl radical having from 1 to 5 carbon atoms, a linear or branched alkoxy radical having from 1 to 4 carbon atoms, a cycloaliphatic radical having 5 or 6 carbon atoms, or an aromatic radical, which cyclic radical can possess one or several lower alkyl radicals as substituents;

or wherein b. two adjacent symbols amongst the $R^1$ to $R^4$ symbols are taken together to represent a saturated or unsaturated ring having 5 or 6 carbon atoms, which ring can possess one or several lower alkyl radicals as substituents, and the other two symbols represent hydrogen.

By a lower alkyl radical it is meant here a $C_1$ to $C_4$, linear or branched, alkyl radical and, more particularly, a methyl or ethyl radical.

PRIOR ART

The compounds of formula (I) are analogues of 3H-benzo[b]furan-2-one, a compound of well-known structure. Furthermore, the structure of several compounds obeying formula (I) is also known from the prior art and several benzofuran-2(3H)-ones are known to possess therapeutical properties, namely as anti-inflamatory agents (see, for example, O. Piccolo et al., J. Chem. Res. 1985, 258). However, in spite of the interest that these compounds have aroused in the pharmaceutical field, we have been unable to find in the prior art any description, or even suggestion, related to the potential usefulness of such compounds in perfumery. Quite clearly, the odor properties of these compounds have gone totally unnoticed up until now.

DESCRIPTION OF THE INVENTION

Yet, we have now discovered that the compounds of formula (I) possess very useful odor properties and that, as a result, they can be used to prepare perfuming compositions and perfumed articles of varied nature.

The odor notes of compounds (I) do in fact cover a very wide spectrum of odoriferous nuances. Whereas certain compounds (I) develop a dominant note of the lactonic, coumarinic, hay type, reminiscent of the odor of flouve and the typical character of tonka beans, others develop notes which are rather lactonic and wherein the fruity, apricot-like character is dominant, or still other compounds develop a musky type odor, recalling the odor of the nitromusks (musk ketone, musk ambrette, etc), or a phenolic, crystalmoss type odor. In fact, certain compounds develop odors in which several of these characters are mixed.

It is therefore apparent that the use of compounds (I) in perfumery makes it possible to obtain a variety of perfuming effects and that these compounds can serve to impart or enhance the coumarinic, lactonic-fruity or even musky notes of the compositions into which they are incorporated.

The odor properties of these compounds are all the more surprising in that they are not represented in a similar way in other families of compounds whose structure is nevertheless very close to that of compounds (I). Thus, for example, we have observed that homologues of these compounds which do not possess a substituent in position 3 of the lactonic ring, or which have two substituents in the same position, turn out to be poor perfuming ingredients when compared to the corresponding compound (I), or are even totally devoid of an olfactive character. We have thus repeatedly observed that the presence of a single substituent in position 3 of the basic molecular skeleton, i.e. of the 3H-benzo[b]furan-2-one type structure, appeared to be a required condition for these compounds to possess useful odor properties.

In this context, one can cite the case of 3,6-dimethyl-3H-benzo[b]furan-2-one, the use of which in perfumery is preferred according to the invention. This lactone develops a very powerful coumarinic note, with a sweet, hay-like character reminiscent of the odor of flouve, as well as a vanilla and tonka type note. Yet, this combination of odor characters, and in particular the strength of the coumarinic-tonka character which renders this compound particularly precious for an alternative use to that of coumarine, is not represented in the weakly coumarinic and phenolic odor of 3,3,6-trimethyl-3H-benzo[b]furan-2-one, and even less in that of 3-ethyl-3,6-dimethyl-3H-benzo[b]furan-2-one, which possesses a disagreable odor typical of hydrocarbons. Moreover, it turned out that this hydrocarbon odor is also characteristic of the note of 3,6-dimethyl-3-propyl-3H-benzo[b]furan-2-one, whereas 3-butyl-3,6-dimethyl-3H-benzo[b]furan-2-one possesses a very weak odor with a vaguely lactonic character.

The same kind of behaviour was observed between 6-isopropyl-3-methyl-3H-benzo[b]furan-2-one and its higher homologues doubly substituted in position 3. This novel lactone is thus a preferred compound of the invention, its odor being representative of the lactonic, fruity, apricot type dominant notes above-cited, accompanied in this case by a slightly phenolic undernote. It is in fact a very tenacious odor, recalling that of decalactone and Veloutone (2,2,5-trimethyl-5-pentyl-1-cyclopentanone; origin: Firmenich SA, Geneva, Switzerland). It was with surprise that the expert perfumers discovered that this olfactive richness had entirely disappeared in 6-isopropyl-3,3-dimethyl-3H-benzo[b]furan-2-one, devoid of olfactive character, or yet in 3-ethyl-6-isopropyl-3-methyl-3H-benzo[b]furan-2-one, 6-isopropyl-3-methyl-3-propyl-benzo[b]furan-2-one and 3-butyl-6-isopropyl-3-methyl-3H-benzo[b]furan-2-one, all of which possess very weak odors, with a vaguely musky or lactonic character.

The surprising olfactive superiority of compounds (I) with regard to their homologues was also very obvious in the case of 5,7-diisopropyl-3-methyl-3H-benzo[b]furan-2-one and of 5,7-di-tert-butyl-3-methyl-3H-benzo[b]furan-2-one. These two novel compounds, which are preferred objects of the invention, possess odors which are typical of the third olfactive family discovered amongst the compounds of the invention, i.e. the odors with a musky character. These odors are all the more unexpected in that they are of the nitromusk type, in spite of the absence of nitrogen-containing groups in the molecule. In particular, the above-mentioned di-tertbutylated lactone possesses a very powerful musky odor, reminiscent of that of the xylol and Baur musks. Another aspect of its musky note is also reminiscent of the odor of the musk ketone. This compound is in fact a choice perfuming ingredient and its olfactive value revealed itself as even richer upon its use in admixture with 3-methyl-cyclopentadec-5-en-1-one (see U.S. Pat. No. 5,354,735) or yet with other musky ingredients which do not possess the characteristic notes of the so-called "nitromusks", such as for example Tonalid® (7-acetyl-1,1,3,4,4,6-hexamethyltetraline; origin: PFW, Holland).

Again, in both cases, their lower homologues non-methylated in position 3, to wit 5,7-diisopropyl-3H-benzo[b]furan-2-one and 5,7-di-tert-butyl-3H-benzo[b]furan-2-one, as well as their di-methylated homologues, or 5,7-diisopropyl-3,3-dimethyl-3H-benzo[b]furan-2-one and 5,7-di-tert-butyl-3,3-dimethyl-3H-benzo[b]furan-2-one, have much too weak odors, devoid of a well-defined olfactive character.

Many other examples of the surprising olfactive behaviour of compounds (I) were observed. On the other hand, in addition to the remarkable range of odor nuances observed, certains types of lactones amongst the compounds (I) seemed to be the object of a particular preference from the perfumers.

In this context, there can be cited the compounds of formula

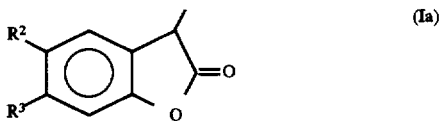

(Ia)

wherein symbols $R^2$ and $R^3$ are identical or different and represent each a hydrogen atom or a $C_1$ to $C_4$ linear or branched alkyl or alkoxy radical, a cycloaliphatic radical having 5 or 6 carbon atoms or an aromatic radical, wherein this cyclic radical can possess one or several lower alkyl radicals as substituents.

Examples of choice ingredients obeying formula (Ia) have already been cited, and others are indicated in Table I further on. As preferred ingredients, there will still be cited 3-methyl-6-phenyl-3H-benzo[b]furan-2-one whose lactonic, fruity, apricot, slightly fatty odor, reminiscent of that of the δ-lactones, of γ-undecalactone and of Veloutone, and in particular its extraordinary tenacity, render it a particularly prized ingredient. The uncommon tenacity of the odor of this compound, the intensity of which remained unchanged on a smelling strip for more than a year, goes in fact far beyond that of any lactone known heretofore and renders this compound extremely advantageous for the typical applications of the cited known lactones.

Other useful examples amongst compounds (I), particularly preferred examples of which have already been cited, are the lactones of formula

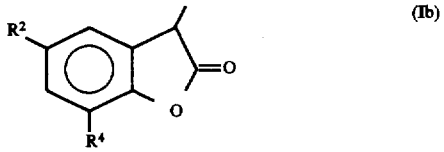

(Ib)

wherein $R^2$ and $R^4$ are identical or different and represent each a linear or branched $C_1$ to $C_4$ alkyl or alkoxy radical, a cycloaliphatic radical having 5 or 6 carbon atoms or an aromatic radical, which cyclic radical can possess one or several lower alkyl radicals as substituents.

Finally, table I hereafter cites yet other preferred compounds and their olfactive characters.

TABLE I

| No | Compound | Odor properties |
|---|---|---|
| 1 | 3-methyl-5-propyl-3H-benzo[b]furan-2-one | lactonic, hay, flouve, bran |
| 2 | 5-tert-butyl-3-methyl-3H-benzo[b]furan-2-one | lactonic, powdery, woody, moss, particularly tenacious, reminiscent of p-tert-butyl-cyclohexyl acetate |
| 3 | 3-methyl-5-(1-methylpropyl)-3H-benzo[b]furan-one | lactonic, fruity, peach and raspberry, with a vanillic undernote, very powerful |
| 4 | 6-methoxy-3-methyl-3H-benzo[b]furan-2-one | coumarinic, hay, flouve, powerful; bottom note slightly phenolic |
| 5 | 3,6,7-trimethyl-3H-benzo[b]furan-2-one | coumarinic, lactonic, slightly peach, slight phenolic nuance, with a powerful bottom note |
| 6 | 3,5,6-trimethyl-3H-benzo[b]furan-2-one | coumarinic, lactonic, coconut |
| 7 | 3,4,6-trimethyl-3H-benzo[b]furan-2-one | coumarinic, reminiscent of the odor of bitter almonds, benzoic, pleasant |
| 8 | 3,5,6,7-tetrahydro-3-methyl-indeno[5,6-b]furan-2-one | lactonic, powerful, coconut, flouve; bottom note, coumarinic, tonka |
| 9 | 3-methyl-3H-benzo[b]furan-one | tonka, coumarinic-dry, powerful benzoic, sweet |
| 10 | 6-ethyl-3-methyl-3H-benzo[b]furan-2-one | lactonic, coumarinic, slightly phenolic, crystalmoss, reminiscent of the odor of lilac and Florex ®[1]) |

[1])9(10)-ethylidene-3-oxatricyclo[6.2.1.0$^{2,7}$]undecan-4-one; origin: Firmenich SA, Geneva, Switzerland As a result of their odor properties, compounds (I) are perfuming ingredients well adapted to both fine and technical perfumery applications. They are advantageous for the preparation of perfuming bases and compositions, perfumes and colognes, as well as for perfuming a variety of products such as soaps, bath or shower gels, shampoos and other hair-care products, body or air-deodorants and cosmetic preparations. One can also use them advantageously for perfuming detergents and fabric softeners, as well as household products.

In these applications, they can be used alone or, as is more current in the art, in admixture with other perfuming ingredients, solvents or adjuvants of current use in perfumery.

The concentrations in which they can be used depend on the nature of the desired fragrance effect, and on the nature of the coingredients with which they are admixed in the perfuming compositions and perfumed articles which contain them. Moreover, given the variety of odor nuances that can be found amongst compounds (I) and the spectrum of the corresponding odor intensities, it is clear that these concentrations will also depend on the nature of the compound (I) used. These concentrations can therefore vary in a very wide range of values, from which there can be cited, strictly by way of example, concentrations of the order of 1 to 10%, or even 20% or more by weight, relative to the weight of the composition into which they are incorporated, and this upon their use for preparing perfuming bases and compositions. Much lower concentration values will generally be used when these compounds serve to perfume the varied consumer products previously cited.

The perfuming compositions and perfumed articles containing compounds (I) and namely the preferred compounds already mentioned, are also the object of the invention.

In spite of the fact that several compounds obeying formula (I) are already known, frequently as a result of citations within the context of organic synthesis or relating to activities in the pharmacological field, there are many amongst these compounds which are novel chemical entities the useful odor properties of which could not have been anticipated from the prior art.

Another object of the invention is therefore a compound of formula

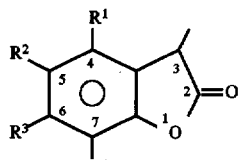
(I)

such as defined in claim 1a., provided that the following combinations are excluded:

a. $R^1=R^2=R^3=R^4=H$;

b. $R^1=R^2=R^4=H$ and $R^3$=methyl or methoxy or phenyl or 2-methylpropyl or cyclopentyl or cyclohexyl;

c. $R^1=R^3=R^4=H$ and $R^2$=methyl or ethyl or phenyl;

d. $R^1=R^4=H$, $R^2=CH_3$ and $R^3$=cyclopentyl or cyclohexyl;

e. $R^1=R^4=H$, $R^2$=phenyl and $R^3$=methoxy; and f. $R^1=R^3$=methoxy, $R^2=CH_3$ and $R^4=H$;

or such as defined in claim 1b., but excluding 1,5,8-trimethyl-1H-naphto[2,1-b]furan-2-one, 3-methyl-3H-naphto[2,3-b]furan-2-one and 1-methyl-1H-naphto [2,1-b]furan-2-one.

In addition, the invention relates in particular to the compounds selected from the group consisting of a. 6-ethyl-3-methyl-3H-benzo[b]furan-2-one;

b. 6-isopropyl-3-methyl-3H-benzo[b]furan-2-one;

c. 3-methyl-5-propyl-3H-benzo[b]furan-2-one;

d. 5-tert-butyl-3-methyl-3H-benzo[b]furan-2-one;

e. 3-methyl-5-(1-methylpropyl)-3H-benzo[b]furan-2-one;

f. 3,4,6-trimethyl-3H-benzo[b]furan-2-one;

g. 3,5,6-trimethyl-3H-benzo[b]furan-2-one;

h. 3,6,7-trimethyl-3H-benzo[b]furan-2-one;

i. 3,5,6,7-tetrahydro-3-methyl-indeno[5,6-b]furan-2-one;

j. 5,7-diisopropyl-3-methyl-3H-benzo[b]furan-2-one; and k. 5,7-di-tert-butyl-3-methyl-3H-benzo[b]furan-2-one.

The compounds of formula (I) can be prepared starting from phenolic derivatives which are either commercially available or which can be easily prepared from commercially available products. The starting phenolic derivatives can be converted in a manner analogous to the method described by O. Piccolo et al., cited ref., which is schematically represented as follows:

Scheme I

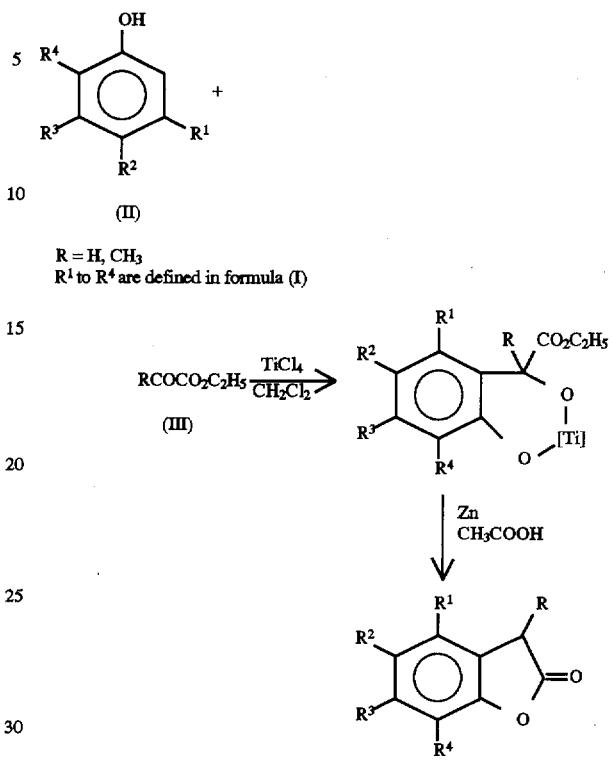

The formula (III) α-keto-ester wherein R=H, $CH_3$ is a commercial product.

Alternatively, and starting from the same phenolic derivatives of formula (II), compounds (I) can be prepared according to an original process which is also the object of the invention, characterized by the reaction of a phenolic derivative of formula

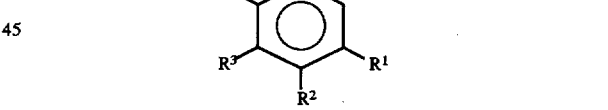
(II)

wherein symbols $R^1$ to $R^4$ are defined as in formula (I), with methylglyoxal, in the presence of an acidic catalyst and in an organic solvent susceptible of forming an azeotropic mixture with water.

The process of the invention is based on an original modification of the process described by R. W. Layer in J. Heterocycl. Chem. 12, 1067 (1975), represented in the following scheme:

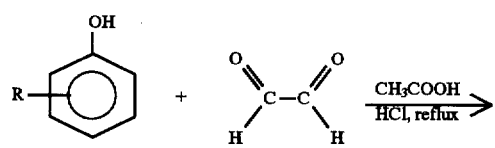

-continued

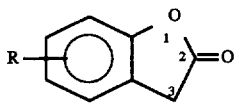

We have established that, unlike the process of the invention, this known method did not enable the preparation, in an efficient manner, of the compounds having a lactonic ring substituted in position 3. One could then observe, in fact, the formation of a major amount of non-useful high molecular weight products.

Surprisingly, we discovered that when the reaction was carried out in an organic solvent capable of forming an azeotropic mixture with water, thus enabling elimination of the latter, the problem observed with the above-mentioned known process was solved.

As the acidic catalyst in the process according to the invention, there can be used an organic or a mineral acid of current use in this function, or yet an acidic resin. Preferably, sulfonic acids will be used, for example p-toluenesulfonic acid or sulfonic resins such asAmberlyst® (origin: Rohm & Haas Co.) or Dowex® (origin: Dow Chem. Co).

The organic solvents that can be used in this process belong to the hydrocarbons family, namely toluene, benzene, cyclohexane or yet xylene, or to that of the currently used chlorinated solvents. Very good yields were obtained with toluene, for example.

The reaction can be carried out at atmospheric pressure and at the solvent's reflux temperature, or under vacuum at a temperature adapted to the azeotropic distillation of water.

The phenolic derivatives of formula (II), as well as methylglyoxal, used as starting products, can be commercially obtained or easily prepared starting from commercial products, following conventional methods.

The invention will now be described in further detail by way of the following examples, wherein the temperatures are indicated in degrees centigrade and the abbreviations have the usual meaning in the art.

EMBODIMENTS OF THE INVENTION

EXAMPLE 1

Preparation of compounds (I)
General method I (according to Circerio et al.)
The method described by O. Piccolo et al., cited ref., page 259 and by A. Citterio et al., Synthesis, 1984, page 763 was followed in an analogous manner, using the starting phenols indicated in the following table. The compounds were purified by means of the usual techniques, i.e. chromatography, distillation, etc. The homologues of compounds (I) non-methylated in position 3 are prepared in an analogous manner (see scheme I).
General method II (according to the invention)
A three-neck flask equipped with a Dean-Stark type water separator, a thermometer and an inlet funnel, is charged with 0.1 mole of phenol, 150 ml of toluene and 1.0 g of p-toluenesulfonic acid. The mixture is heated to reflux (110°) and 0.1 mole of methylglyoxal (40% aqueous solutions, Fluka) is slowly introduced (over 1h30) while maintaining reflux to eliminate the water. The mixture is heated to reflux for yet 1 h, then cooled to room temperature, the organic phase is washed with a saturated solution of NaHCO$_3$, then with water to neutrality, dried over Na$_2$SO$_4$, concentrated and purified by column chromatography (SiO$_2$) and distillation or crystallization, depending on the case.

Of course, when methylglyoxal is replaced by glyoxal in this process, there are again obtained the corresponding lower homologues of the compounds of the invention, i.e. the lactones which are not substituted in position 3 of the lactonic ring.

On the other hand, the higher homologues of compounds (I) which are di-substituted in position 3 are prepared by alkylation, under known conditions, of the appropriate compounds of the invention.

Several of these homologue compounds, selected namely amongst those cited above, are also described hereinafter.

The following Table II cites the compounds prepared and their odor properties:

TABLE II

| No | Starting product | Final product | Odor properties of the final product |
|---|---|---|---|
| 1 | phenol | compound 9, Table I | see Table 1 |
| 2 | 4-methylphenol | 3,5-dimethyl-3H-benzo[b]furan-2-one | strongly crystalmoss phenolic, slightly coumarinic |
| 3 | 3-methylphenol | 3,6-dimethyl-3H-benzo[b]furan-2-one | see above |
| 4 | 2-methylphenol | 3,7-dimethyl-3H-benzo[b]furan-2-one | dry, crystalmoss, seaweed |
| 5 | 3-ethylphenol | compound 10, Table I | see Table I |
| 6 | 4-ethylphenol | 5-ethyl-3-methyl-3H-benzo[b]furan-2-one | crystalmoss, phenolic |
| 7 | 4-propylphenol | compound 1, Table I | see Table I |
| 8 | 3-isopropylphenol | 6-isopropyl-3-methyl-3H-benzo[b]furan-2-one | see above |
| 9 | 4-isopropylphenol | 5-isopropyl-3-methyl-3H-benzo[b]furan-2-one | phenolic, thyme leaves, lactonic |
| 10 | 3-tert-butylphenol | 6-tert-butyl-3-methyl 3-H-benzo[b]furan-2-one | sweet, vanillic |
| 11 | 4-tert-butylphenol | compound 2, Table I | see Table I |
| 12 | 4-(1-methylpropyl)-phenol | compound 3, Table I | see Table I |
| 13 | 3-methoxyphenol | compound 4, Table I | see Table I |
| 14 | 4-methoxyphenol | 5-methoxy-3-methyl-3H-benzo[b]furan-2-one | phenolic, weakly coumarinic, vanillic |
| 15 | 2,3-dimethylphenol | compound 5, Table I | see Table I |
| 16 | 2,4-dimethylphenol | 3,5,7-trimethyl-3H-benzo[b]furan-2-one | Florex ®, coumarinic lactonic, flouve, rhubarb-metallic, fatty |
| 17 | 3,4-dimethylphenol | compound 6, Table I | see Table I |
| 18 | 3,5-dimethylphenol | compound 7, Table I | see Table I |
| 19 | 2,4,5-trimethyl-phenol | 3,4,6,7-tetramethyl-3H-benzo[b]furan-2-one | phenolic, waxy |
| 20 | 3-phenylphenol | 3-methyl-6-phenyl-3H-benzo[b]furan-2-one | see above |
| 21 | 2-phenylphenol | 3-methyl-7-phenyl-3H-benzo[b]furan-2-one | phenolic, coumarinic |
| 22 | 5,6,7,8-tetrahydro-1-naphthalenol | 6,7,8,9-tetrahydro-3-methyl-3H-naphtho[1,2-b]furan-2-one | vaguely humus; bottom note coumarinic, flouve, phenolic |
| 23 | 5-indanol | compound 8, Table I | see Table 1 |
| 24 | 3,4,5,6-tetrahydro-3,3,4α,5β,6,6-hexamethyl-1-naphthalenol | 5,6,7,8-tetrahydro-3,5,5,6α7β,8,8-heptamethyl-3H-naphtho[2,3-b]furan-2-one | vaguely musky lactonic; bottom note musky |
| 25 | 2,4-di-tert-butyl phenyl | 5,7-di-tert-butyl-3-methyl-3H-benzo[b]furan-2-one | see above |
| 26 | 2,4-di-tert-butyl-3-phenol | 5,7-di-tert-butyl-3H benzo[b]furan-2-one | vaguely musky |
| 27 | 5,7-di-tert-butyl-3-methyl-3H- | 5,7-di-tert-butyl-3,3-dimethyl-3H- | weak, without olfactive character |

TABLE II-continued

| No | Starting product | Final product | Odor properties of the final product |
|---|---|---|---|
| | benzo[b]furan-2-one | benzo[b]furan-2-one | |
| 28 | 2,4-diisoprophyl-phenol (see H.) Jendralla et al., Synthesis 1990, 827) | 5,7-diisopropyl-3H-benzo[b]furan-2-one | without olfactive character |
| 29 | 2,4-diisopropyl-phenol | 5,7-diisopropyl-3-methyl-3H-benzo[b]furan-2-one | see above |
| 30 | 5,7-diisopropyl-3-methyl-3H-benzo[b]furan-2-one | 5,7-diisopropyl-3,3-dimethyl-3H-benzo[b]furan-2-one | without olfactive character |
| 31 | 2-tert-butyl-4-ethyl-phenol | 7-tert-butyl-5-ethyl-3-methyl-3H-benzo[b]furan-2-one | lactonic, coconut, peach-slightly hay-like |
| 32 | 4-(1,1-dimethylpropyl)-phenol | 5-(1,1-dimethylpropyl)-3-methyl-3H-benzo[b]furan-2-one | raspberry, strawberry, liqueur |
| 33 | 2-tert-butyl-phenol | 7-tert-butyl-3-methyl-3H-benzo[b]furan-2-one | green, pyrazines, peas |
| 34 | 3,6-dimethyl-3H-benzo[b]furan-2-one | 3,3,6-trimethyl-3H-benzo[b]furan-2-one | see above |
| 35 | 6-isopropyl-3-methyl-3H-benzo[b]furan-2-one | 6-isopropyl-3,3-dimethy-3H-benzo[b]furan-2-one | see above |
| 36 | 6-isopropyl-3-methyl-3H-benzo[b]furan-2-one | 6-isopropyl-3-methyl-3-propyl-3H-benzo[b]furan-2-one | see above |

The analytical characteristics of the compounds cited in this Table are described hereinafter following the same order:

Compound 1

| | |
|---|---|
| Purity: | 99.8% |
| MS: | M$^+$148(98); m/e: 133(2), 120(96), 103(4), 91 (100), 77(10), 65(14), 51(15), 39(12) |
| $^1$H-NMR (360 MHz, CDCl$_3$): | 1.57(d: J=7, 3H), 3.72(q: J=7, 1H), 7.06–7.36 (m, 4H) δ ppm |
| $^{13}$C-NMR (90 MHz, CDCl$_3$): | 1q: 15.9; 5d: 38.4, 110.7, 123.9, 124.2, 128.8; 3s: 128.8, 153.5, 177.9 δ ppm |

Compound 2

| | |
|---|---|
| Purity | 99.7% |
| M.p. | 37.5–39° |
| MS: | M$^+$162(72); m/e: 147(1), 134(100), 119(15), 105 (14), 91(46), 77(14), 65(10), 51(12), 39(10) |
| $^1$H-NMR (360 MHz, CDCl$_3$): | 1.56(d: J=7, 3H), 2.35(s, 3H), 3.68(q: J=7, 1H), 6.97 (d: J=7, 1H), 7.07(m, 2H) δ ppm |
| $^{13}$C-NMR (90 MHz, CDCl$_3$): | 2q: 15.9, 21.1; 4d: 38.5, 110.3, 124.4, 129.1; 4s: 128.7, 133.8, 151.4, 178.3 δ ppm |

Compound 3

| | |
|---|---|
| Purity | 99.8% |
| M.p. | 41.5–43° |
| MS: | M$^+$162(82); m/e: 147(2), 134(100), 119(22), 105 (16), 91(58), 77(14), 65(12), 51(12), 39(14) |
| $^1$H-NMR (360 MHz, CDCl$_3$): | 1.53(d: J=7, 3H), 2.37(s, 3H), 3.67(q: J=7, 1H), 6.90(s, 1H), 6.95(d: J=7, 1H), 7.12(d: J=7, 1H) δ ppm |
| $^{13}$C-NMR (90 MHz, CDCl$_3$): | 2q: 16.0, 21.6; 4d: 38.2, 111.3, 123.5, 124.8; 4s: 125.8, 139.2, 153.6, 178.3 δ ppm |

Compound 4

| | |
|---|---|
| Purity | 99.9% |
| M.p. | 33.5–35° |
| MS: | M$^+$162(70); m/e: 147(1), 134(100), 119(20), 105 (15), 91(54), 77(14), 65(10), 51(12), 39(12) |
| $^1$H-NMR(360 MHz, CDCl$_3$): | 1.56(d: J=7, 3H), 2.32(s, 3H), 3.72(q: J=7, 1H), 7.01–7.12(m, 3H) δ ppm |
| $^{13}$C-NMR(90 MHz, CDCl$_3$): | 2q: 15.1, 15.9; 4d: 38.8, 121.1, 124.0, 130.2; 4s: 121.0, 128.4, 152.0, 178.2 δ ppm |

Compound 5

| | |
|---|---|
| Purity | 98.7% |
| MS: | M$^+$176(45); m/e: 161(2), 148(66), 133(100), 115 (8), 105(22), 91(17), 77(20), 65(12), 51(14), 39 (20) |
| $^1$H-NMR(360 MHz, CDCl$_3$): | 1.24(t: J=7, 3H), 1.55(d: J=7, 3H), 2.67(q: J=7, 2H), 3.68(q: J=7, 1H), 6.95(s, 1H), 6.98(d: J=7, 1H), 7.15(d: J=7, 1H) δ ppm |
| $^{13}$C-NMR(90 MHz, CDCl$_3$): | 2q: 15.6, 16.0; 1t: 29.1; 4d: 38.3, 110.1, 2×123.6; 4s: 126.0, 145.7, 153.7, 178.4 δ ppm |

-continued

Compound 6

| | |
|---|---|
| Purity | 99.1% |
| MS: | $M^+$176(31); m/e: 161(2), 148(30), 133(100), 115 (4), 105(8), 91(11), 77(16), 65(8), 51(12), 39(12) |
| $^1$H-NMR(360 MHz, CDCl$_3$): | 1.23(t: J=7, 3H), 1.57(d: J=7, 3H), 2.64(q: J=7, 2H), 3.70(q: J=7, 1H), 6.99(d: J=7, 1H), 7.10(m, 2H) δ ppm |
| $^{13}$C-NMR(90 MHz, CDCl$_3$): | 2q: 15.9, 16.0; 1t: 28.6; 4d: 38.5, 110.3, 123.3, 128.0; 4s: 128.8, 140.4, 151.5, 178.3 δ ppm |

Compound 7

| | |
|---|---|
| Purity | 99.2% |
| MS: | $M^+$190(17); m/e: 161(14), 146(1), 133(100), 115 (4), 103(5), 91(5), 77(7), 65(2), 51(2), 39(1) |
| $^1$H-NMR(360 MHz, CDCl$_3$): | 0.94(t: J=7, 3H), 1.57(d: J=7, 3H), 1.63(m, 2H), 2.58(t: J=7, 2H), 3.70(q: J=7, 1H), 6.99(d: J=7, 1H), 7.07(m, 2H) δ ppm |
| $^{13}$C-NMR(90 MHz, CDCl$_3$): | 2q: 13.7, 15.9; 2t: 24.9, 37.7; 4d: 38.5, 110.2, 123.8, 128.7; 4s: 128.6, 138.8, 151.6, 178.3 δ ppm |

Compound 8

| | |
|---|---|
| Purity | 99.4% |
| MS: | $M^+$190(44); m/e: 175(12), 162(33), 147(100), 128 (6), 119(14), 103(8), 91(32), 77(14), 65(10), 51(6), 39(8) |
| $^1$H-NMR(360 MHz, CDCl$_3$): | 1.25(d: J=7, 6H), 1.55(d: J=7, 3H), 2.93(sept.: J=7, 1H), 3.69(q: J=7, 1H), 6.97(s, 1H), 7.01(d: J=7, 1H), 7.17(d: J=7, 1H) δ ppm |
| $^{13}$C-NMR(90 MHz, CDCl$_3$): | 3q: 15.9; 2×24.0; 5d: 34.4, 38.3, 128.6, 122.3, 123.6; 4s: 126.1, 150.5, 153.7, 178.3 δ ppm |

Compound 9

| | |
|---|---|
| Purity | 99.4% |
| MS: | $M^+$190(20); m/e: 175(24), 162(8), 147(100), 128 (4), 115(6), 103(4), 91(16), 77(8), 65(4), 51(3), 39 (2) |
| $^1$H-NMR(360 MHz, CDCl$_3$): | 1.25(d: J=7, 6H), 1.57(d: J=7, 3H), 2.91(sept.: J=7, 1H), 3.70(q: J=7, 1H), 7.01(d: J=7, 1H), 7.13(m, 2H) δ ppm |
| $^{13}$C-NMR(90 MHz, CDCl$_3$): | 3q: 15.9; 2×24.3; 5d: 34.0, 38.6, 110.3, 121.8, 126.6; 4s: 128.7, 145.1, 151.6, 178.3 δ ppm |

Compound 10

| | |
|---|---|
| Purity | 99.3% |
| M.p. | 73–75° |
| MS: | $M^+$204(30); m/e: 189(84), 176(6), 161(100), 146 (5), 133(29), 115(18), 105(12), 91(21), 77(10), 65 (6), 51(4), 41(4) |
| $^1$H-NMR(360 MHz, CDCl$_3$): | 1.32(s, 9H), 1.54(d: J=7, 3H), 3.67(q: J=7, 1H), 7.11–7.20(m, 3H) δ ppm |
| $^{13}$C-NMR(90 MHz, CDCl$_3$): | 4q: 15.9, 3×31.3; 4d: 38.2, 107.9, 121.0, 123.3; 5s: 35.1, 125.7, 152.9, 153.6, 178.3 δ ppm |

Compound 11

| | |
|---|---|
| Purity | 100% |
| M.p. | 71–72° |
| MS: | $M^+$204(28); m/e: 189(88), 161(100), 146(3), 133 (14), 115(8), 105(5), 91(10), 77(6), 65(4), 51(4), 41(5) |
| $^1$H-NMR(360 MHz, CDCl$_3$): | 1.33(s, 9H), 1.58(d: J=7, 3H), 3.70(q: J=7, 1H), 7.01(d: J=7, 1H), 7.27(s, 1H), 7.31(d: J=7, 1H) δ ppm |
| $^{13}$C-NMR(90 MHz, CDCl$_3$): | 4q: 15.9, 3×31.6; 4d: 38.7, 110.0, 120.8, 125.6; 5s: 34.7, 128.3, 147.4, 151.3, 178.4 δ ppm |

Compound 12

| | |
|---|---|
| | (1:1 mixture of two diastereoisomers) |
| Purity | 98.1% |
| MS: | $M^+$204(18); m/e: 189(2), 175(79), 161(5), 147 (100), 133(8), 115(8), 103(4), 91(14), 77(6), 65 (3), 51(2), 39(2) |
| $^1$H-NMR(360 MHz, CDCl$_3$): | 0.83(t: J=7, 3H), 2.23(d: J=7, 3H), 1.57(d: J=7, 3H), 1.60(m, 2H), 2.49(hex.: J=7, 1H), 3.70(q: J=7, 1H), 6.96–7.13(m, 3H) δ ppm |
| $^{13}$C-NMR(90 MHz, CDCl$_3$): | 3q: 12.2, 15.9, 22.0/22.1; 1t: 31.3/31.4; 5d: 38.6, 41.5, 110.3, 122.3/122.4, 127.2/127.3; 4s: 128.7, 143.9, 151.6, 178.3 δ ppm |

Compound 13

| | |
|---|---|
| Purity | 96.5% |

-continued

| | |
|---|---|
| M.p. | 33–35° |
| MS: | M⁺178(64); m/e: 163(12), 150(100), 135(20), 121 (17), 107(22), 91(22), 77(26), 65(12), 51(10), 39 (8) |
| ¹H-NMR(360 MHz, CDCl₃): | 1.53(d: J=7, 3H), 3.67(q: J=7, 1H), 3.80(s, 3H), 6.65(s, 1H), 6.67(d: J=7, 1H), 7.13(d: J=7, 1H) δ ppm |
| ¹³C-NMR(90 MHz, CDCl₃): | 2q: 16.2, 55.6; 4d: 38.0, 97.5, 109.7, 124.3; 4s: 120.5, 154.4, 160.4, 178.4 δ ppm |

Compound 14

| | |
|---|---|
| Purity | 99.5% |
| M.p. | 63–65° |
| MS: | M⁺178(48); m/e: 163(1), 150(92), 135(100), 121 (3), 107(20), 91(10), 77(30), 63(11), 53(20), 39 (14) |
| ¹H-NMR(360 MHz, CDCl₃): | 1.57(d: J=7, 3H), 3.71(q: J=7, 1H), 3.80(s, 3H), 6.81(m, 2H), 7.01(d: J=7, 1H) δ ppm |
| ¹³C-NMR(90 MHz, CDCl₃): | 2q: 15.9, 55.9; 4d: 39.0, 110.2, 111.1, 113.5; 4s: 129.8, 147.3, 156.7, 178.3 δ ppm |

Compound 15

| | |
|---|---|
| Purity | 99.8% |
| MS: | M⁺176(47); m/e: 161(2), 148(100), 133(53), 115 (16), 105(62), 91(26), 77(22), 65(10), 51(10), 39(8) |
| ¹H-NMR(360 MHz, CDCl₃): | 1.54(d: J=7, 3H), 2.22(s, 3H), 2.29(s, 3H), 3.71 (q: J=7, 1H), 6.93(d: J=7, 1H), 6.97(d: 7, 1H) δ ppm |
| ¹³C-NMR(90 MHz, CDCl₃): | 3q: 11.8, 16.1, 19.6; 3d: 39.0, 120.5, 125.1; 5s: 119.7, 125.8, 137.9, 152.2, 178.5 δ ppm |

Compound 16

| | |
|---|---|
| Purity | 99.3% |
| M.p. | 30–32° |
| MS: | M⁺176(46); m/e: 161(1), 148(100), 133(58), 115 (12), 105(54), 91(24), 77(24), 65(10), 51(10), 39 (10) |
| ¹H-NMR(360 MHz, CDCl₃): | 1.53(d: J=7, 3H), 2.27(s, 3H), 2.31(s, 3H), 3.67 (q: J=7, 1H), 6.87(s, 1H), 6.90(s, 1H) δ ppm |
| ¹³C-NMR(90 MHz, CDCl₃): | 3q: 14.9, 16.0, 21.0; 3d: 38.9, 121.6, 130.7; 5s: 120.5, 128.3, 133.5, 149.9, 178.5 δ ppm |

Compound 17

| | |
|---|---|
| Purity | 100% |
| M.p. | 74–75° |
| MS: | M⁺176(60); m/e: 161(2), 148(100), 133(66), 115 (10), 105(40), 91(17), 77(16), 65(5), 51(4), 39(4) |
| ¹H-NMR(360 MHz, CDCl₃): | 1.51(d: J=7, 3H), 2.23(s, 3H), 2.25(s, 3H), 3.62 (q: J=7, 1H), 6.84(s, 1H), 7.00(s, 1H) δ ppm |
| ¹³C-NMR(90 MHz, CDCl₃): | 3q: 16.0, 19.4, 20.1; 3d: 38.3, 111.6, 124.8; 5s: 126.0, 132.2, 137.3, 151.8, 178.5 δ ppm |

Compound 18

| | |
|---|---|
| Purity | 99.8% |
| M.p. | 66–68° |
| MS: | M⁺176(69); m/e: 161(8), 148(100), 133(70), 115 (18), 105(80), 91(26), 77(29), 65(11), 51(12), 39 (13) |
| ¹H-NMR(360 MHz, CDCl₃): | 1.56(d: J=7, 3H), 2.29(s, 3H), 2.32(s, 3H), 3.64 (q: J=7, 1H), 6.73(s, 1H), 6.75(s, 1H) δ ppm |
| ¹³C-NMR(90 MHz, CDCl₃): | 3q: 15.6, 18.2, 21.5; 3d: 38.0, 108.8, 126.3; 5s: 124.0, 134.5, 138.9, 153.6, 178.5 δ ppm |

Compound 19

| | |
|---|---|
| Purity | 100% |
| M.p. | 49–51° |
| MS: | M⁺190(54); m/e: 175(5), 162(100), 147(78), 129 (9), 119(56), 105(10), 91(32), 77(17), 65(10), 51 (7), 39(8) |
| ¹H-NMR(360 MHz, CDCl₃): | 1.57(d: J=7, 3H), 2.17(s, 3H), 2.24(s, 3H), 2.26(s, 3H), 3.67(q: J=7, 1H), 6.73(s, 1H) δ ppm |
| ¹³C-NMR(90 MHz, CDCl₃): | 4q: 11.6, 15.7, 17.9, 19.4; 2d: 38.8, 126.6; 6s: 116.8, 123.9, 131.2, 137.6, 152.0, 178.7 δ ppm |

Compound 20

| | |
|---|---|
| Purity | 99.6% |
| M.p. | 102–104° |
| MS: | M⁺224(62); m/e: 209(2), 196(100), 181(10), 167 (44), 152(36), 139(8), 128(6), 115(12), 102(6), 89 (9), 76(8), 63(5), 51(4), 39(2) |

|  |  |
|---|---|
| $^1$H-NMR(360 MHz, CDCl$_3$): | 1.58(d: J=7, 3H), 3.73(q: J=7, 1H), 7.23–7.58 (m, 8H) δ ppm |
| $^{13}$C-NMR(90 MHz, CDCl$_3$): | 1q: 15.9; 9d: 38.3, 109.4, 123.0, 124.1, 2×127.1, 127.8, 2×128.9; 5s: 127.6, 140.2, 142.5, 154.0, 177.9 δ ppm |

Compound 21

|  |  |
|---|---|
| Purity | 99.3% |
| M.p. | 99–102° |
| MS: | M$^+$224(62); m/e: 196(52), 181(100), 165(22), 152 (30), 139(6), 128(4), 115(12), 98(6), 89(4), 76(6), 63(6), 51(4), 39(4) |
| $^1$H-NMR(360 MHz, CDCl$_3$): | 1.63(d: J=7, 3H), 3.79(q: J=7, 1H), 7.23(m, 2H), 7.37(m, 1H), 7.46(m, 3H), 7.67(m, 2H) δ ppm |
| $^{13}$C-NMR(90 MHz, CDCl$_3$): | 1q: 16.0; 9d: 38.4, 122.7, 124.6, 127.9., 3×128.6, 2× 128.9; 5s: 125.0, 129.5, 135.4, 150.5, 177.9 δ ppm |

Compound 22

|  |  |
|---|---|
| Purity | 98.5% |
| M.p. | 63–65° |
| MS: | M$^+$202(60); m/e: 187(1), 174(100), 159(66), 145 (28), 131(33), 115(33), 103(10), 91(22), 77(16), 65 (8), 51(8), 39(6) |
| $^1$H-NMR(360 MHz, CDCl$_3$): | 1.52(d: J=7, 3H), 1.78(m, 4H), 2.72(m, 4H), 3.64 (q: J=7, 1H), 6.85(d: J=7, 1H), 6.96(d: J=7, 1H) δ ppm |
| $^{13}$C-NMR(90 MHz, CDCl$_3$): | 1q: 16.0; 4t: 22.2, 2×22.8, 29.4; 3d: 38.7, 120.3, 124.5; 5s: 120.8, 125.1, 138.5, 151.5, 178.6 δ ppm |

Compound 23

|  |  |
|---|---|
| Purity | 97.6% |
| M.p. | 79–81° |
| MS: | M$^+$188(52); m/e: 173(2), 160(100), 145(18), 133 (14), 115(22), 103(4), 91(12), 77(8), 163(4), 51(4), 39(2) |
| $^1$H-NMR(360 MHz, CDCl$_3$): | 1.53(d: J=7, 3H), 2.10(m, 2H), 2.89(m, 4H), 3.67 (q: J=7, 1H), 6.95(s, 1H), 7.09(s, 1H) δ ppm |
| $^{13}$C-NMR(90 MHz, CDCl$_3$): | 1q: 16.2; 3t: 25.8, 32.4, 33.2; 3d: 38.6, 107.0, 119.6; 5s: 126.6, 139.7, 144.9, 152.1, 178.7 δ ppm |

Compound 24 (1:1 mixture of two diastereoisomers)

|  |  |
|---|---|
| Purity | 98% |
| M.p. | 127–130° |
| MS: | M$^+$286(29); m/e: 271(91), 243(4), 229(48), 215 (100), 201(30), 187(12), 171(6), 157(5), 141(8), 128(10), 115(8), 91(7), 77(6), 57(23), 43(12) |
| $^1$H-NMR(360 MHz, CDCl$_3$): | 0.98(d: J=6, 6H), 1.10(s, 6H), 1.30(s, 6H), 1.57 (m, 5H), 3.68(m, 1H), 7.07(s, 1H), 7.23(s, 1H) δ ppm |
| $^{13}$C-NMR(90 MHz, CDCl$_3$): | 7q: 13.9, 14.0, 15.9/16.0, 25.6/25.7, 25.8, 29.6/29.8, 29.8/29.9; 5d: 38.4/38.5, 39.1, 39.2, 108.4, 122.4/122.5; 7s: 2×38.0, 126.2, 141.7, 146.9, 151.6, 178.6 δ ppm |

Compound 25

|  |  |
|---|---|
| Purity | 99.6% |
| M.p. | 62–64° |
| MS: | M$^+$260(26); m/e: 245(100), 232(2), 217(70), 201 (2), 189(2), 175(2), 159(2), 145(2), 128(4), 115 (6), 105(4), 91(6), 77(4), 57(9), 41(5) |
| $^1$H-NMR(360 MHz, CDCl$_3$): | 1.33(s, 9H), 1.40(s, 9H), 1.57(d: 7, 3H), 3.67 (q: J=7, 1H), 7.11(s, 1H), 7.27(s, 1H) δ ppm |
| $^{13}$C-NMR(90 MHz, CDCl$_3$): | 7q: 15.9, 3×29.6, 3×31.6; 3d: 38.2, 118.2, 122.8; 7s: 34.4, 34.8, 128.6, 133.3, 147.0, 149.2, 178.6 δ ppm |

Compound 26

|  |  |
|---|---|
| Purity | 99.6% |
| M.p. | 89–92° |
| MS: | M$^+$246(22); m/e: 231(100), 217(1), 203(52), 188 (2), 175(3), 161(6), 145(7), 128(6), 115(10), 105 (8), 91(12), 80(9), 65(4), 57(6), 41(8) |
| $^1$H-NMR(360 MHz, CDCl$_3$): | 1.32(s, 9H), 1.40(s, 9H), 3.68(s, 2H), 7.15(s, 1H), 7.26(s, 1H) δ ppm |
| $^{13}$C-NMR(90 MHz, CDCl$_3$): | 6q: 3×29.6, 3×31.6; 1t: 32.9; 2d: 119.1, 122.7; 7s: 34.3, 34.7, 123.0, 133.3, 146.8, 150.5, 174.5 δ ppm |

Compound 27

|  |  |
|---|---|
| Purity | 99.3% |
| M.p. | 114–115° |
| MS: | M$^+$274(26); m/e: 259(90), 231(100), 215(4), 201 |

-continued

| | |
|---|---|
| | (2), 189(2), 173(2), 159(2), 141(4), 128(6), 115 (7), 108(7), 94(9), 80(10), 65(4), 57(18), 41(14) |
| ¹H-NMR(360 MHz, CDCl₃): | 1.33(s, 9H), 1.40(s, 9H), 1.49(s, 6H), 7.05(split s, 1H), 7.26(split s, 1H) δ ppm |
| ¹³C-NMR(90 MHz, CDCl₃): | 8q: 2×25.5, 3×29.7, 3×31.7, 2d: 116.9, 122.6; 8s: 34.4, 34.9, 42.5, 133.3, 133.5, 147.1, 147.9, 181.6 δ ppm |

Compound 28

| | |
|---|---|
| Purity: | 99.5% |
| M.p. | 29–31° |
| MS: | M⁺218(41); m/e: 203(100), 190(4), 175(89), 159 (3), 147(27), 131(6), 119(14), 105(13), 91(19), 77 (13), 65(7), 51(6), 41(10) |
| ¹H-NMR(360 MHz, CDCl₃): | 1.23(d: J=7, 6H), 1.28(d: J=7, 6H), 2.88(sept.: J=7, 1H), 3.15(sept.: J=7, 1H), 3.69(s, 2H), 6.98 (s, 1H) δ ppm |
| ¹³C-NMR(90 MHz, CDCl₃): | 4q: 2×22.4, 2×24.3; 1t: 33.4; 4d: 28.8, 34.1, 119.6, 124.4; 5s: 122.7, 131.4, 145.1, 150.4, 174.8 δ ppm |

Compound 29

| | |
|---|---|
| Purity | 99.5% |
| MS: | M⁺232(27); m/e: 217(32), 204(16), 189(100), 175 (3), 161(13), 147(6), 128(8), 115(10), 105(5), 91 (13), 77(8), 65(4), 53(4), 41(9) |
| ¹H-NMR(360 MHz, CDCl₃): | 1.24(d: J=7, 6H), 1.29(split d: J=7, 6H), 1.57(d: J=7, 3H), 2.49(sept.: J=7, 1H), 3.15(sept.: J=7, 1H), 3.69(q: J=7, 1H), 6.93(s, 1H), 7.01(s, 1H) δ ppm |
| ¹³C-NMR(90 MHz, CDCl₃): | 5q: 15.91 22.3, 22.5, 24.3, 24.4; 5d: 28.8, 34.1, 38.8, 118.8, 124.3; 5s: 128.4, 131.3, 145.1, 149.1, 178.7 δ ppm |

Compound 30

| | |
|---|---|
| Purity | 99.3% |
| M.p. | 34–37° |
| MS: | M⁺246(29); m/e: 231(21), 218(24), 203(100), 187 (2), 175(8), 161(3), 147(3), 128(7), 115(8), 105 (5), 91(8), 80(6), 65(4), 53(3), 41(9) |
| ¹H-NMR(360 MHz, CDCl₃): | 1.25(d: J=7, 6H), 1.29(d: J=7, 6H), 1.49(s, 6H), 2.90(sept.: J=7, 1H), 3.17(sept.: J=7, 1H), 6.88 (split s, 1H), 7.00(split s, 1H) δ ppm |
| ¹³C-NMR(90 MHz, CDCl₃): | 6q: 2×22.5, 2×24.3, 2×25.5; 4d: 28.7, 34.2, 117.7, 124.0; 6s: 43.2, 131.4, 133.3, 145.2, 147.8, 181.7 δ ppm |

Compound 31

| | |
|---|---|
| Purity: | 99.8% |
| M.p. | 57–58° |
| MS: | M⁺232(24); m/e: 217(30), 204(6), 189(100), 175 (10), 161(16), 141(4), 128(8), 115(8), 105(5), 91 (10), 77(6), 65(4), 53(2), 41(4) |
| ¹H-NMR(360 MHz, CDCl₃): | 1.23(t: J=7, 3H), 1.39(s, 9H), 1.56(d: J=7, 3H), 2.63(q: J=7, 2H), 3.65(q: J=7, 1H), 6.93(s, 1H), 7.05(s, 1H) δ ppm |
| ¹³C-NMR(90 MHz, CDCl₃): | 5q: 15.9, 16.0, 3×29.6; 1t: 28.8; 3d: 38.0, 120.6, 125.4; 6s: 34.2, 129.2, 133.8, 140.0, 149.4, 178.5 δ ppm |

Compound 32

| | |
|---|---|
| Purity | 96.8% |
| M.p. | 30–32° |
| MS: | M⁺218(10); m/e: 203(4), 189(100), 175(4), 161 (88), 145(4), 133(20), 115(10), 105(6), 91(12), 77 (6), 65(3), 55(2), 41(3) |
| ¹H-NMR(360 MHz, CDCl₃): | 0.69(t: J=7, 3H), 1.28(s, 6H), 1.59(d: J=7, 3H), 1.63(q: J=7, 2H), 3.71(q: J=7, 1H), 7.01(d: J=7, 1H), 7.20(s, 1H), 7.25(d: J=7, 1H) δ ppm |
| ¹³C-NMR(90 MHz, CDCl₃): | 3q: 9.1, 16.0, 28.7; 1t: 37.0; 4d: 38.7, 109.9, 121.4, 126.3; 5s: 37.9, 128.3, 145.8, 151.3, 178.4 δ ppm |

Compound 33

| | |
|---|---|
| Purity: | 98.3% |
| MS: | M⁺204(21); m/e: 189(34), 176(1), 161(100), 147 (4), 133(26), 115(10), 105(6), 91(10), 77(6), 65 (3), 51(2), 39(2) |
| ¹H-NMR(360 MHz, CDCl₃): | 1.40(s, 9H), 1.57(d: J=7, 3H), 3.69(q: J=7, 1H), 7.07-7.27(m, 3H) δ ppm |
| ¹³C-NMR(90 MHz, CDCl₃): | 4q: 15.9, 3×29.6; 4d: 37.9, 121.4, 124.0, 125.9; 5s: 34.2, 129.2, 134.4, 151.4, 178.1 δ ppm |

-continued

Compound 34

| | |
|---|---|
| Purity | 99.9% |
| MS: | M⁺176(60); m/e: 161(14), 148(100), 133(69), 115 (15), 105(58), 91(16), 77(24), 63(10), 51(14), 39 (18) |
| ¹H-NMR(360 MHz, CDCl₃): | 1.47(s, 6H), 2.37(s, 3H), 6.93(s, 1H), 6.96(d: J=7, 1H), 7.09(d: J=7, 1H) δ ppm |
| ¹³C-NMR(90 MHz, CDCl₃): | 3q: 21.6, 2×25.3; 3d: 111.4, 122.4, 124.9; 5s: 42.8, 130.7, 138.9, 152.3, 181.2 δ ppm |

Compound 35

| | |
|---|---|
| Purity | 99.9% |
| M.p. | 77–78° |
| MS: | M⁺204(39); m/e: 189(16), 176(64), 161(100), 145 (4), 133(15), 115(13), 105(9), 91(16), 77(12), 65 (8), 51(8), 41(14) |
| ¹H-NMR(360 MHz, CDCl₃): | 1.26(d: J=7, 6H), 1.48(s, 6H), 2.93(sept.: J=7, 1H), 6.99(s, 1H), 7.02(d: J=7, 1H), 7.12(d: J=7, 1H) δ ppm |
| ¹³C-NMR(90 MHz, CDCl₃): | 4q: 2×24.0, 2×25.3; 4d: 34.4, 108.8, 2×122.4; 5s: 42.9, 130.9, 150.2, 152.4, 181.4 δ ppm |

Compound 36

| | |
|---|---|
| Purity | 99.9% |
| MS: | M⁺232(30); m/e: 217(3), 204(5), 189(100), 175 (14), 161(36), 147(26), 133(10), 115(13), 105(9), 91(16), 77(8), 65(5), 51(4), 41(14) |
| ¹H-NMR(360 MHz, CDCl₃): | 0.83(t: J=7, 3H), 0.93–1.22(m, 2H), 1.27(d: J=7, 6H), 1.47(s, 3H), 1.75(m, 1H), 1.90(m, 1H), 2.93 (sept.: J=7, 1H), 6.97(split s, 1H), 7.01(split d, 7, 1H), 7.08(d: J=7, 1H) δ ppm |
| ¹³C-NMR(90 MHz, CDCl₃): | 4q: 14.0, 2×24.0, 24.4; 2t: 18.1, 41.4; 4d: 34.3, 108.6, 122.3, 122.7; 5s: 47.4, 129.4, 150.1, 152.9, 181.0 δ ppm |

EXAMPLE 2

Preparation of a perfuming composition

A base perfuming composition intended for a perfume of the masculine, oriental type, was prepared by admixing the following ingredients:

| Ingredients | Parts by weight |
|---|---|
| Linalyly acetate | 210 |
| 10%* Ambrox ® DL[1] | 350 |
| Dist. methyl anthranilate | 25 |
| 10%* 4(4-Hydroxyphenyl)-2-butanone | 15 |
| Synth. bergamot oil | 135 |
| 10%* Ceylan cinnamon oil | 70 |
| 10%* Eugenol | 40 |
| Lemon essential oil | 110 |
| Heliotropine ord. | 120 |
| Hydroxycitronellal | 35 |
| 10%* Purif. indol | 15 |
| Polywood ®[2] | 190 |
| Dihydromyrcenol[3] | 180 |
| Linalol | 50 |
| Lyral ®[4] | 400 |
| Synth. mandarin oil | 30 |
| Iralia ®[5] | 90 |
| Methylnaphthylketone cryst. | 20 |
| Methyl jasmonate | 300 |
| Patchouli essential oil | 120 |
| Sandalore ®[6] | 50 |
| Tonalid ®[7] | 500 |
| Exaltolide ®[8] | 200 |
| Vanilline | 95 |
| Vertofix coeur[9] | 250 |
| TOTAL | 3600 |

-continued

| Ingredients | Parts by weight |
|---|---|

*in dipropyleneglycol (DIPG)
[1] tetramethyl-perhydronaphthofuran, origin: Firmenich SA, Geneva, Switzerland
[2] perhydro-5,5,8a-trimethyl-2-naphthyl acetate; origin: Firmenich SA, Geneva, Switzerland
[3] origin: International Flavors and Fragrances Inc., U.S.A.
[4] 4-(4-hydroxy-4-methylpentyl)-3-cyclohexene-1-carboxaldehyde; origin: International Flavors and Fragrances Inc., U.S.A.
[5] methylionone; origin: Firmenich SA, Geneva, Switzerland
[6] 5-(2,2,3-trimethylcyclopent-3-enyl)-3-methylpentan-2-ol; origin: Givaudan-Roure, Vernier, Switzerland
[7] 7-acetyl-1,1,3,4,4,6-hexamethyltetraline; origin: PFW, Holland
[8] pentadecanolide; origin: Firmenich SA, Geneva, Switzerland
[9] origin: International Flavors and Fragrances Inc., U.S.A.

When there were added to this base composition of the balsamic, floral, woody, musky type, 400 parts by weight of 3,6-dimethyl-3H-benzo[b]furan-2-one, there was obtained a novel composition with a distinctly enhanced oriental, coumarinic-vanilla note, with a well-defined tonka character and a clearly enhanced strength. This coumarinic olfactive effect, which was also observed at lower concentrations of the compound of the invention, of the order of a half or even a quarter of the cited amount, ressembles the effect that could have been obtained with coumarine, although the tonka beans type of note was more marked.

Similar effects, albeit with varied nuances, were obtained when the same amount of other compounds according to the invention, having a coumarinic odor, was added. For example, 3-methyl-3H-benzo[b]furan-2-one imparted an odor of the same type, but drier and sweeter, whereas 6-methoxy-3-methyl-3H-benzo[b]furan-2-one imparted to the composition a coumarinic odor with an enhanced phenolic character. The addition of 3,5,6,7-tetrahydro-3-methyl-indeno[5,6-b]furan-2-one also emphasized the coumarinic-tonka note in the odor of the new composition, with a coconut type top character, which could also be found when there was added 3,5,6-trimethyl-3H-benzo[b]furan-2-one to the base composition, whereas 3,4,6-trimethyl-3H-benzo[b]furan-2-one imparted a coumarinic-bitter almond note instead to this composition.

EXAMPLE 3

Perfuming of textiles

There were prepared samples of a perfumed softener base by adding to distinct samples of an unperfumed standard fabric softener the compounds according to the invention cited in the following Table, in the amounts indicated:

| Ingredients | Sample | | | | | | |
|---|---|---|---|---|---|---|---|
| | 1 | 2 | 3 | 4 | 5 | 6 | 7 |
| unperfumed softener | 99.9 | 99.9 | 99.9 | 99.9 | 99.9 | 99.9 | 99.9 |
| 3,6-dimethyl-3H-benzo[b]furan-2-one | 0.1 | — | — | — | — | — | — |
| 6-isopropyl-3-methyl-3H-benzo[b]furan-2-one | — | 0.1 | — | — | — | — | — |
| 3-methyl-6-phenyl-3H-benzo[b]furan-2-one | — | — | 0.1 | — | — | — | — |
| 6-ethyl-3-methyl-3H-benzo[b]furan-2-one | — | — | — | 0.1 | — | — | — |
| 6-methoxy-3-methyl-3H-benzo[b]furan-2-one | — | — | — | — | 0.1 | — | — |
| 5,7-diisopropyl-3-methyl-3H-benzo[b]furan-2-one | — | — | — | — | — | 0.1 | — |
| 5,7-di-tert-butyl-3-methyl-3H-benzo[b]furan-2-one | — | — | — | — | — | — | 0.1 |

Seven batches of standard textiles, containing cotton, acrylic and nylon fabrics, were separately treated in seven fabric washing machines with respectively samples 1 to 7 prepared above. The seven textile batches thus treated were then evaluated on a blind test by a panel of expert perfumers, both wet and after drying.

According to the perfumers, three distinct fragrance effects could be observed. Thus, the textiles treated with samples 1, 4 and 5 developed an odor having a dominant coumarinic character, very powerful in the case of the batch treated with sample 1, with a distinctly marked hay, flouve and tonka character, whereas the batch treated with sample 4 developed an odor wherein the lactonic, crystalmoss character was more pronounced and which was also more phenolic.

As for the textiles treated with samples 2 and 3, their odor no longer had a dominant coumarinic character, but rather lactonic and fruity, very pleasant, recalling the fragrance developed by Veloutone (origin: Firmenich SA, Geneva, Switzerland) and the decalactones, and whose fruity note was similar to the odor of apricot. Furthermore, the textiles treated with sample 3 turned out to have a particularly tenacious odor, which stayed on the linen for a long time.

On the other hand, the batches treated with samples 6 and 7 were judged to be entirely different from the others, their odor being strongly musky and not at all coumarinic nor lactonic-fruity, with a much appreciated nitromusk type character.

This effect was all the more pronounced in the textiles perfumed by means of sample 7, and this both when just out of the machine and 24 h later. The perfumers judged that these variations in the observed odor effects were totally surprising when they found out the nature of the perfuming ingredients used and the similarity of their structures.

EXAMPLE 4

Perfuming composition

A base perfuming composition intended for a powder detergent was prepared by admixing the following ingredients:

| Ingredients | Parts by weight |
|---|---|
| Benzyl acetate | 50 |
| Linalyl acetate | 20 |
| Phenylethyl acetate | 40 |
| Verdyl acetate | 100 |
| 10%* Undecylenic aldehyde | 70 |
| Hexylcinnamic aldehyde | 80 |
| 10%* Methyl benzoate | 50 |
| Eugenol | 25 |
| Helional | 50 |
| 10%* 4,4a,5,9b-Tetrahydro-indeno[1,2-d]-1,3-dioxine | 50 |
| Iralia ®[1] | 60 |
| Iso E Super[2] | 40 |
| Lilial ®[3] | 400 |
| Linalol | 100 |
| 10%* Methylacetophenone | 20 |
| 10%* Methyl-p-cresol | 10 |
| 10%* Rose oxide | 5 |
| 10%* Phenylethyl methyl ether | 10 |
| Phenethylol | 210 |
| p-tert-Butyl-cyclohexanone acetate | 170 |
| Benzyl salicylate | 30 |
| Tonalid ®[4] | 160 |
| TOTAL | 1750 |

*in dipropyleneglycol (DIPG)
[1] methylionone; origin: Firmenich SA, Geneva, Switzerland
[2] 2-acetyl-1,2,3,4,6,7,8-octahydro-2,3,8,8-tetramethyl-naphthalene; origin: IFF, USA
[3] 2-methyl-3-(4-tert-butyl-1-phenyl)-propanal; origin: Givaudan-Roure, Vernier, Switzerland
[4] 7-acetyl-1,1,3,4,4,6-hexamethyltetraline; origin: PFW, Holland 250 Parts by weight of 5,7-di-tert-butyl-3-methyl-3H-benzo[b]furan-2-one were added to this base composition. A novel composition was thus obtained, the musky, earthy, aromatic note of which, imparted by Tonalid®, was distinctly enhanced relative to that of the base composition, its odor having become musky-animal and clearly evoking the typical fragrance effect that could have been obtained by adding Musk Xylol to the base composition.

On the other hand, when the base composition contained, instead of Tonalid®, 60 parts by weight of 3-methyl-cyclopentadec-5-en-1-one (see U.S. Pat. No. 5,354,735), thus having already a musky, nitromusk and powdery character, the addition of 350 parts by weight of the above-mentioned compound of the invention made it possible to obtain a novel composition wherein the above-mentioned olfactive effect was even more obvious, the odor of the composition being even more reminiscent of the fragrance that can be obtained with such known compounds as Musk Xylol, Musk Baur or yet Musk ketone.

Furthermore, when 250 parts by weight of 5,7-diisopropyl-3-methyl-3H-benzo[b]furan-2-one were added to the composition instead of the compound of the invention cited above, similar but slightly less pronounced odor effects were observed.

EXAMPLE 5

Perfuming composition

A base perfuming composition was prepared by admixing the following ingredients

| Ingredients | Parts by weight |
|---|---|
| Synth. amber oil | 100 |
| Bergamot essential oil | 100 |
| Exaltex ®¹⁾ | 80 |
| Iralia ®²⁾ | 100 |
| 50%* Oakmoss absolute | 270 |
| Crystalmoss | 50 |
| Portugal Italy orange essential oil | 40 |
| Patchouli essential oil | 70 |
| Bourbon vetyver essential oil | 80 |
| Wardia ®³⁾ | 80 |
| TOTAL | 970 |

*in dipropyleneglycol (DIPG)
¹⁾oxacyclohexadecan-2-one; origin: Firmenich SA, Geneva, Switzerland
²⁾methylionone; origin: Firmenich SA, Geneva, Switzerland
³⁾origin: Firmenich SA, Geneva, Switzerland When 30 parts by weight of 3-methyl-6-phenyl-3H-benzo[b]furan-2-one were added to this base composition of the Chypre type, there was obtained a novel composition, the odor of which had acquired a distinct fruity-lactonic character reminiscent of the classical perfumes such as "Madame" of Rochas or "Champagne" of Yves St. Laurent.

On the other hand, when the effect imparted by this compound was compared to that obtained by adding to the base composition 30 parts by weight of γ-undecalactone, it became apparent that the resulting composition according to the invention possessed a more pronounced fruity, apricot type note, whereas that of the composition which contained γ-undecalactone possessed a weaker fruity character which was rather of the peach type. In addition, after 24 h, the fruity note was far more perceptible in the odor of the composition containing 3-methyl-6-phenyl-3H-benzo[b]furan-2-one and a week later it was still persistent, without any change in its strength, whereas no fruity character could any longer be perceived in the odor of the composition which contained γ-undecalactone.

The addition of 30 parts by weight of 6-isopropyl-3-methyl-3H-benzo[b]furan-2-one to the base composition provided a novel composition whose odor possessed a more marked lactonic character than in the case of the addition of its phenyl analogue, although the volume and the tenacity of the odor were nevertheless inferior.

We claim:

1. A method for imparting a fragrance to a composition or article which comprises adding to said composition or article a perfuming ingredient comprising a compound of formula

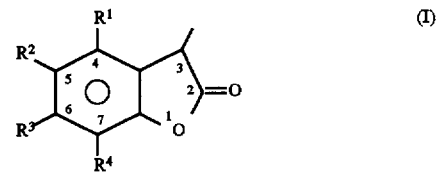

wherein
a. symbols $R^1$ to $R^4$ represent hydrogen; or
b. $R^1$ represents hydrogen, one of $R^2$, $R^3$ or $R^4$ represents a linear or branched alkyl radical having from 1 to 5 carbons, a methoxy group, a cycloaliphatic radical having 5 or 6 carbon atoms or a phenyl radical, and the others represent hydrogen; or
c. $R^1$ represents hydrogen and two adjacent symbols among $R^2$ and $R^4$ are identical or different and each represent a $C^1$ to $C^4$ linear or branched alkyl radical or a methoxy group, with the other symbol representing hydrogen; or
d. two non-adjacent symbols among $R^1$ to $R^4$ represent hydrogen and the other two are identical or different and represent a $C^1$ to $C^4$ linear or branched alkyl radical or a methoxy group; or
e. two adjacent symbols among $R^1$ to $R^4$ are taken together to represent a saturated or unsaturated ring having 5 or 6 carbon atoms, which ring can possess one or more methyl radicals as substituents, with the other two symbols representing hydrogen; or
f. one of symbols among $R^1$ to $R^4$ is hydrogen and the other three are identical and represent a methyl group;

said compound added in an amount effective to impart, modify or enhance the odor character of said composition or article.

2. The method according to claim 1 wherein the perfuming ingredient is a compound of formula

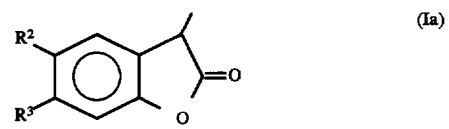

wherein $R^2$ and $R^3$ are identical or different and each represents a hydrogen atom, a $C_1$ to $C_4$ linear or branched alkyl radical, or a methoxy group.

3. The method according to claim 1 wherein the perfuming ingredient is a compound of formula

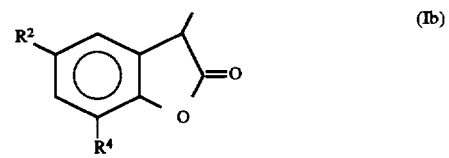

wherein $R^2$ and $R^4$ are identical or different and each represents a hydrogen atom, a $C_1$ to $C_4$ linear or branched alkyl radical, or a methoxy group.

4. The method according to claim 1 wherein the perfuming ingredient is 3,4,6-trimethyl-3H-benzo[b]furan-2-one, 3,6,7-trimethyl-3H-benzo[b]furan-2-one or 3,5,6,7-tetrahydro-3-methyl-indeno[5,6-b]furan-2-one.

5. The method according to claim 1 wherein the perfuming ingredient is one of the following compounds:
   a. 3-methyl-3H-benzo[b]furan-2-one;
   b. 3,6-dimethyl-3H-benzo[b]furan-2-one;
   c. 6-ethyl-3-methyl-3H-benzo[b]furan-2-one;
   d. 6-isopropyl-3-methyl-3H-benzo[b]furan-2-one;
   e. 3-methyl-6-phenyl-3H-benzo[b]furan-2-one;
   f. 6-methoxy-3-methyl-3H-benzo[b]furan-2-one;
   g. 3-methyl-5-propyl-3H-benzo[b]furan-2-one;
   h. 5-tert-butyl-3-methyl-3H-benzo[b]furan-2-one;
   i. 3-methyl-5-(1-methylpropyl)-3H-benzo[b]furan-2-one; or
   j. 3,5,6-trimethyl-3H-benzo[b]furan-2-one.

6. The method according to claim 3 wherein the perfuming ingredient is 5,7-diisopropyl-3-methyl-3H-benzo[b]furan-2-one or 5,7-di-tert-butyl-3-methyl-3H-benzo[b]furan-2-one.

7. The method according to claim 6 wherein the perfuming ingredient is 5,7-di-tert-butyl-3-methyl-3H-benzo[b]furan-2-one in admixture with 3-methyl-cyclopentadec-5-en-1-one.

8. Perfuming composition or perfumed article containing as an active perfuming ingredient a compound of formula (I), (Ia) or (Ib) as defined in one of claims 1, 2 or 3.

9. Perfuming composition or perfumed article containing as an active perfuming ingredient one of the compounds recited in one of claims 4, 5 or 6.

10. Perfuming composition or perfumed article containing as an active perfuming ingredient the admixture of compounds recited in claim 7.

11. Perfumed article produced by the method of claim 1 in the form of a perfume or cologne, a soap, a bath or shower gel, a shampoo or other hair care product, a cosmetic preparation, a body or air deodorant, a detergent, a fabric softener or a household product.

12. A the compound selected from the group consisting of:
   a. 6-ethyl-3-methyl-3H-benzo[b]furan-2-one;
   b. 6-isopropyl-3-methyl-3H-benzo[b]furan-2-one;
   c. 3-methyl-5-propyl-3H-benzo[b]furan-2-one;
   d. 5-tert-butyl-3-methyl-3H-benzo[b]furan-2-one;
   e. 3-methyl-5-(1-methylpropyl)-3H-benzo[b]furan-2-one;
   f. 3,4,6-trimethyl-3H-benzo[b]furan-2-one;
   g. 3,5,6-trimethyl-3H-benzo[b]furan-2-one;
   h. 3,6,7-trimethyl-3H-benzo[b]furan-2-one;
   i. 3,5,6,7-tetrahydro-3-methyl-indeno[5,6-b]furan-2-one;
   j. 5,7-diisopropyl-3-methyl-3H-benzo[b]furan-2-one; and
   k. 5,7-di-tert-butyl-3-methyl-3H-benzo[b]furan-2-one.

* * * * *